United States Patent
Murdeshwar et al.

(10) Patent No.: US 9,198,719 B2
(45) Date of Patent: Dec. 1, 2015

(54) ELECTROSURGICAL FIBROID ABLATION SYSTEM AND METHOD

(71) Applicant: GYRUS ACMI, INC., Southborough, MA (US)

(72) Inventors: Nikhil M. Murdeshwar, Maple Grove, MN (US); Jeffrey J. Nelson, Maple Grove, MN (US)

(73) Assignee: GYRUS ACMI, INC., Southborough, MA (US)

( * ) Notice: Subject to any disclaimer, the term of this patent is extended or adjusted under 35 U.S.C. 154(b) by 166 days.

(21) Appl. No.: 14/041,641

(22) Filed: Sep. 30, 2013

(65) Prior Publication Data

US 2015/0094712 A1 Apr. 2, 2015

(51) Int. Cl.
*A61B 18/14* (2006.01)
*A61B 17/34* (2006.01)
(Continued)

(52) U.S. Cl.
CPC ......... *A61B 18/1477* (2013.01); *A61B 17/3415* (2013.01); *A61B 18/1492* (2013.01); *A61B 2018/00023* (2013.01); *A61B 2018/00559* (2013.01); *A61B 2018/00577* (2013.01); *A61B 2018/00642* (2013.01); *A61B 2018/00702* (2013.01); *A61B 2018/00714* (2013.01); *A61B 2018/00744* (2013.01); *A61B 2018/00821* (2013.01); *A61B 2018/126* (2013.01); *A61B 2018/1467* (2013.01); *A61B 2018/1475* (2013.01)

(58) Field of Classification Search
CPC ............. A61B 2018/00559; A61B 2018/1475; A61B 18/1477
See application file for complete search history.

(56) References Cited

U.S. PATENT DOCUMENTS 5,531,676 A * 7/1996 Edwards et al. ............... 604/22
6,090,105 A 7/2000 Zepeda et al.
6,379,349 B1 4/2002 Muller et al.
(Continued)

FOREIGN PATENT DOCUMENTS

| WO | WO 2008/016922 A2 | 2/2008 |
| WO | WO 2010/099481 A1 | 9/2010 |
| WO | WO 2011/161474 A1 | 12/2011 |

OTHER PUBLICATIONS

Gokhan Goynumer et al., "Spontaneous uterine rupture during a second trimester pregnancy with a history of laparoscopic myomectomy", Journal of Obstetrics and Gynaecology Research, vol. 35, No. 6, Dec. 1, 2009, pp. 1132-1135, XP055136179, ISSN: 1341-8076, 001: 10.1111 Ij.1447-0756.2009.01 070.x.
(Continued)

*Primary Examiner* — Joseph Stoklosa
*Assistant Examiner* — Jocelyn D Ram
(74) *Attorney, Agent, or Firm* — Oliff PLC

(57) ABSTRACT

Electrosurgical fibroid ablation systems and methods utilize a probe having at least two electrodes to perform bipolar ablation. The probe is inserted into a uterine fibroid so as to enter the fibroid along the major-axis direction of an ellipsoidal fibroid (a direction that is substantially parallel to the uterine wall). Inserting the probe in this direction facilitates ablation of the fibroid with a single probe penetration because the area of ablation tends to progress within a volume having an ellipsoidal shape that is aligned with the ellipsoidal shape of the fibroid. Furthermore, any scar left by the procedure tends to extend in a direction that is parallel to the uterine wall, and thus is less likely to propagate and cause rupture of the uterine wall during pregnancy.

11 Claims, 5 Drawing Sheets

(51) Int. Cl.
  *A61B 18/00* (2006.01)
  *A61B 18/12* (2006.01)

(56) References Cited

U.S. PATENT DOCUMENTS

| | | | |
|---|---|---|---|
| 6,506,189 | B1 | 1/2003 | Rittman, III et al. |
| 6,572,614 | B1 | 6/2003 | Ellman et al. |
| 7,862,560 | B2 | 1/2011 | Marion |
| 7,918,795 | B2 | 4/2011 | Grossman |
| 2003/0097130 | A1 | 5/2003 | Muller et al. |
| 2004/0167517 | A1 | 8/2004 | Desinger et al. |
| 2006/0189972 | A1* | 8/2006 | Grossman ............. 606/32 |
| 2007/0016183 | A1 | 1/2007 | Lee et al. |
| 2007/0249936 | A1 | 10/2007 | Deckman et al. |
| 2009/0187182 | A1* | 7/2009 | Epstein et al. ........ 606/34 |
| 2009/0204060 | A1 | 8/2009 | Desinger et al. |
| 2009/0221998 | A1* | 9/2009 | Epstein et al. ........ 606/33 |
| 2010/0222677 | A1* | 9/2010 | Placek et al. ........ 600/439 |
| 2010/0324506 | A1* | 12/2010 | Pellegrino et al. ...... 604/272 |
| 2011/0230874 | A1 | 9/2011 | Epstein et al. |

OTHER PUBLICATIONS

Skrablin S et al., "Successful pregnancy after spontaneous rupture of scarred uterus following fundal myomectomy", European Journal of Obstetrics & Gynecology and Reproductivebiology, Excerpta Medica, Amsterdam, NL, vol. 121, No. 2, Aug. 1, 2005, pp. 251-252, XP027604608, ISSN: 0301-2115 [retrieved on Aug. 1, 2005].

Kumakiri J et at., "Prospective Evaluation for the Feasibility and Safety of Vaginal Birth after Laparoscopic Myomectomy", Journal of Minimally Invasive Gynecology, Elsevier, NL, vol. 15, No. 4, Jul. 1, 2008, pp. 420-424, XP022820074, ISSN: 1553-4650, 001: 10.1 016/J.JMIG.2008.04.008, [retrieved on Jul. 2, 2008].

Database Medline [Online] US National Library of Medicine (NLM), Bethesda, MD, US; Sep. 3, 2013, Jia Li-Ying et al., "[Clinical analysis of uterine rupture during pregnancy].", Database accession No. NLM24360052 ; & Zhonghua Yi Xue Za Zhi Sep. 3, 2013, vol. 93, No. 33, Sep. 3, 2013, pp. 2674-2676, ISSN: 0376-2491, Abstract only.

Sep. 22, 2014 Search Report and Written Opinion issued in International Application No, PCT/US2014/039915.

* cited by examiner

ELECTROSURGICAL FIBROID ABLATION SYSTEM AND METHOD

BACKGROUND

This disclosure relates to methods and apparatus for ablating uterine fibroids.

Uterine fibroids are the most common pelvic tumor in women, affecting approximately one quarter of women during their reproductive years. Uterine fibroids are generally noncancerous, but may potentially lead to infertility or cause adverse effects if they occur during pregnancy. Typical symptoms include abnormal bleeding, pressure, or pain.

Uterine fibroids are categorized based on location on the uterus. Sub-mucosal fibroids form on the inside wall of the uterus; sub-serosal fibroids form on the outside wall of the uterus; intra-mural fibroids form within the walls of the uterus; and pedunculated fibroids are connected to the inside or outside wall of the uterus.

Currently uterine fibroid treatments include both pharmaceutical and surgical techniques. Pharmaceutical treatments often do not adequately treat the symptoms of uterine fibroids, ultimately necessitating surgical intervention. Surgical techniques include hysterectomy, myomectomy, endometrial ablation, myolysis, and uterine artery occlusion. In addition, interventional radiology and high frequency focused ultrasound techniques exist for the treatment of uterine fibroids.

All of these treatment techniques suffer from shortcomings, such as the risk of relapse, infertility, and applicability to only one or a few types of uterine fibroids.

SUMMARY

Some uterine fibroid treatments use a probe to insert one or more electrodes into the fibroid to ablate the fibroid. When the electrode(s) is/are activated to apply ablative energy while extending in a direction perpendicular to the uterine wall, the uterine wall will be left with a scar (defect) that extends in the thickness direction of the uterus. Such scars weaken the uterus wall and are prone to propagation and can lead to rupture of the uterine wall during a pregnancy.

Furthermore, because fibroids tend to change shape from spherical to ellipsoidal as they increase in size, and tend to orient themselves with their major (longer) axis parallel to the uterine wall, such ellipsoidal-shaped fibroids need to be penetrated multiple times along their lengths (the length extending in the major-axis direction) in order for the entire fibroid to be effectively ablated. Such multiple penetrations of the fibroid and the uterine wall further weaken the uterine wall, making it even more prone to rupture during a pregnancy.

Aspects of the invention relate to electrosurgical fibroid ablation systems and methods in which a probe having at least two electrodes to perform bipolar ablation is inserted into a uterine fibroid so as to enter the fibroid along the major-axis direction of the fibroid. Inserting the probe in the major-axis direction of the fibroid facilitates ablation of the fibroid with a single probe penetration because the area of ablation tends to progress within a volume having an ellipsoidal shape that is aligned with the ellipsoidal shape of the fibroid. Furthermore, any scar left by the procedure tends to extend in a direction that is parallel to the uterine wall, and thus is less likely to propagate and cause rupture of the uterine wall during pregnancy. Thus, the system and method facilitate uterus preservation even when relatively large fibroids (e.g., having lengths of 3-6 cm) are ablated.

According to some embodiments, an electrosurgical fibroid ablation system includes a catheter and a flexible probe. The catheter (which may be flexible or rigid) includes (i) a sharp distal tip configured to pierce tissue, (ii) a hollow interior, (iii) a sideward-facing exit hole adjacent to the distal tip, and (iv) a sloped guide member adjacent to the exit hole. At least a portion of the sloped guide member is located within the hollow interior of the catheter. The flexible probe is movably disposed within the hollow interior of the catheter, and includes a sharp distal end that can be extended outward of the catheter through the exit hole so as to enter a fibroid when the exit hole of the catheter is positioned adjacent to the fibroid. The distal end of the probe is flexible and includes at least two electrodes to perform bipolar ablation. The sloped guide member deflects the distal end of the probe when the probe is advanced through the catheter so that the distal end of the probe exits the exit hole at a predefined angle relative to the longitudinal axis of the catheter.

According to some embodiments, the predefined angle is approximately a right angle. Accordingly, even if the catheter is inserted into the uterine wall in a direction perpendicular to the uterine wall in order to puncture the uterine wall, the probe will extend in a direction substantially parallel to (along) the uterine wall into the fibroid, thereby leaving a scar that is parallel to the wall, rather than extending in the thickness direction of the wall.

According to some embodiments, the sloped guide member is adjustable to adjust the predefined angle at which the distal end of the probe exits through the exit hole.

According to some embodiments, the flexible distal end of the probe includes a plurality of segments that are movably linked to each other in order to form the flexible distal end of the probe.

The fibroid ablation system can be used by: (1) piercing the wall of the uterus with the sharp distal end of the catheter; (2) positioning the exit hole of the catheter adjacent to one end out of two opposite ends of the fibroid, the ends being separated from each other along a major axis of the fibroid; (3) advancing the probe through the hollow interior of the catheter so that the flexible distal end of the probe exits through the exit hole and is introduced into the fibroid along the major axis of the fibroid at least until the at least two electrodes are positioned within the fibroid; and (4) energizing the at least two electrodes to at least partially ablate the fibroid.

When the fibroid is ellipsoidal in shape, so as to include a minor axis that is shorter than the major axis (the minor axis being substantially perpendicular to the major axis), the probe is advanced into the fibroid along the major axis of the fibroid.

Preferably, once introduced into the fibroid, the distal end of the probe, which includes the at least two electrodes, extends in a direction that is substantially perpendicular to a thickness direction of the wall of the uterus (that is, the distal end extends in a direction parallel to the uterine wall).

Preferably, the probe is inserted into the fibroid a single time to ablate the fibroid, thus reducing scarring.

According to some embodiments, the catheter is transcutaneously introduced into the uterus. According to other embodiments, the catheter is transcervically introduced into the uterus. The mode of insertion depends on the location of the fibroid.

A method for ablating a fibroid in a wall of a uterus of a patient includes the steps of: (1) piercing the wall of the uterus with a sharp distal tip of a catheter; (2) positioning an exit hole of the catheter adjacent to one end out of two opposite ends of the fibroid, the two ends being separated from each other in a direction that is substantially parallel to the wall of the uterus (i.e., in a direction along a major axis of the fibroid when the fibroid is ellipsoidal in shape); (3) advancing a probe through the catheter so that a distal end of the probe exits through the exit hole and is introduced into the fibroid in the direction substantially parallel to the wall of the uterus (i.e., in the direction along the major axis of the fibroid when the fibroid is ellipsoidal in shape) at least until at least two electrodes provided on the distal end of the probe are positioned within the fibroid; and (4) energizing the at least two electrodes to at least partially ablate the fibroid.

According to preferred embodiments, the exit hole of the catheter faces sideward and is located adjacent to the distal tip of the catheter, the catheter also includes a guide member adjacent to the exit hole, and at least a portion of the guide member is located within a hollow interior of the catheter. At least the distal end of the probe having the at least two electrodes is flexible, and thus the guide member deflects the distal end of the probe when the probe is advanced through the catheter so that the distal end of the probe exits the exit hole at a predefined angle relative to the catheter.

BRIEF DESCRIPTION OF THE DRAWINGS

Exemplary embodiments will be described in detail with reference to the following drawings in which.

DETAILED DESCRIPTION OF THE EMBODIMENTS

The following exemplary embodiments are described below with reference to the figures in the context of uterine fibroid treatment, and in particular ablation of uterine fibroids utilizing Radio Frequency Induced Thermotherapy Technology (RFITT).

Figure 1:
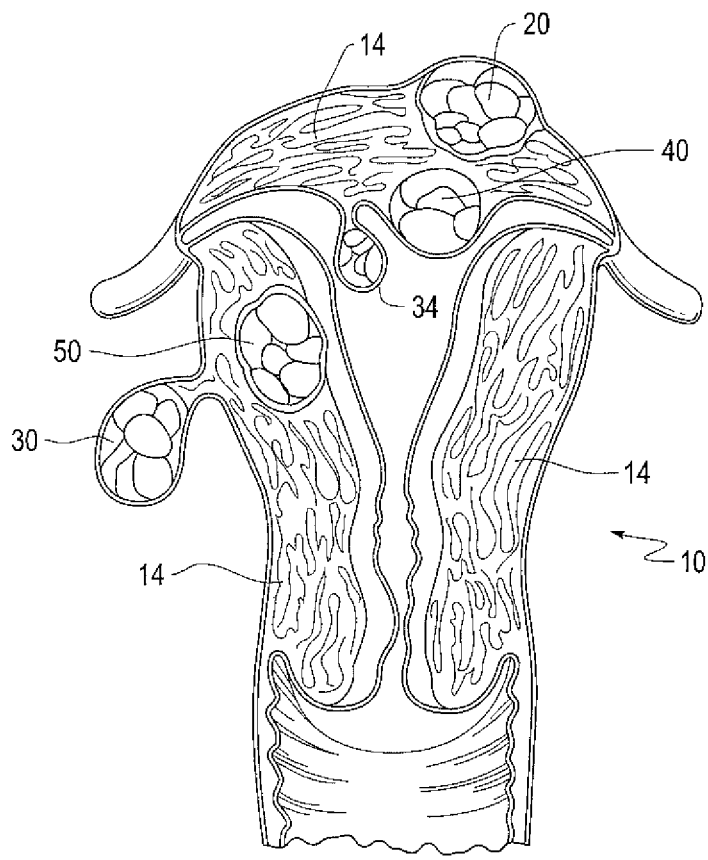
FIG. 1 illustrates various locations of uterine fibroids.

FIG. 1 illustrates different anatomical locations of uterine fibroids that can potentially afflict a patient. A sub-mucosal fibroid 40 is located on the inside wall of the uterus 10. A sub-serosal fibroid 20 is located on the outside wall of the uterus 10. An intra-mural fibroid 50 is located within the wall 14 of the uterus 10. A pedunculated fibroid 30 is attached to the outer wall of the uterus 10. Because it is attached to the outer wall of the uterus 10, fibroid 30 more specifically is known as a pedunculated sub-serosal fibroid. Fibroid 34 is known as a pedunculated sub-mucosal fibroid because it is attached to the inner wall of the uterus 10.

The location, size and orientation of a patient's fibroid(s) is first determined by one or more known imaging techniques.

For example, ultrasonic imaging (known as "ultrasound") can be performed using a transducer placed externally of the patient's body or located within the uterus, for example, at the end of a transcervically inserted ultrasonic probe. MRI also could be used.

Once the location, size and orientation of the (or each) fibroid has been determined, the surgeon will determine how to access the fibroid(s). For example, sub-mucosal fibroids and pedunculated sub-mucosal fibroids typically are accessed transcervically, whereas sub-serosal fibroids, pedunculated sub-serosal fibroids and intra-mural fibroids typically are transcutaneously accessed from the pelvic cavity (i.e., laproscopically accessed). However, the manner of accessing each fibroid also depends on the desired outcome of the surgery (e.g., fertility, resolution of the patient's symptoms, etc.), the size of each fibroid, as well as the location of other fibroids within the uterus.

Figure 2:
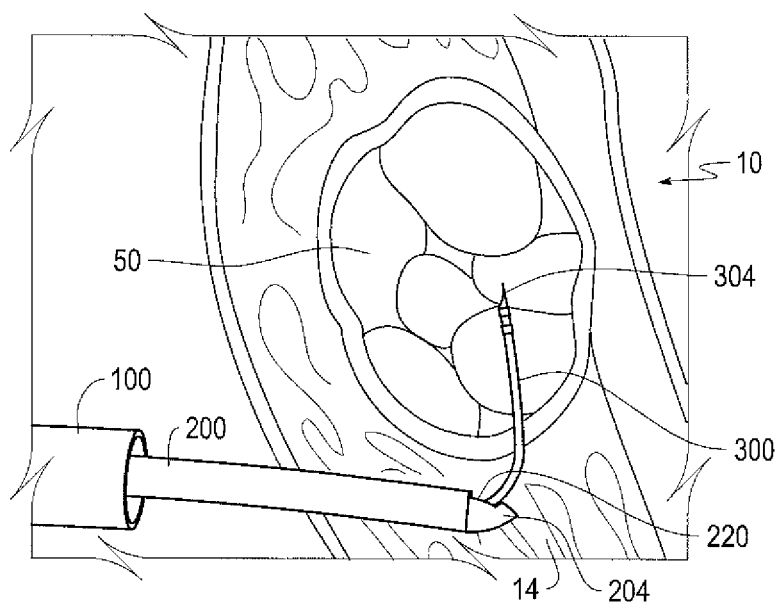
FIG. 2 is a diagram showing the manner in which a sharp-tipped catheter is used to introduce a bipolar ablation probe into a fibroid.

As shown in FIG. 2, a cannula device, for example, an endoscope 100 is used to introduce a sharp-tipped catheter 200 to the location of the fibroid. The endoscope includes a first passage through which the catheter is inserted. The first passage includes a distal opening at or near the distal end of the endoscope 100, and the distal end of the catheter 200 can be manipulated by the surgeon (using a handpiece provided at the proximal end of the catheter 200) to extend from the distal opening of the first passage. The endoscope 100 also typically will include additional passages through which other devices can be introduced to the surgical site. In addition, an optical system and/or an imaging system (such as an ultrasonic transducer) can be provided near the distal end of the endoscope, or provided as separate devices that are introduced to the surgical site through passages of the endoscope. The optical system and/or imaging system is/are used by the surgeon during the procedure to monitor the position of, and thereby precisely position, the catheter 200 and the flexible bipolar probe 300 as described below.

In addition, an external imaging system, for example, an ultrasonic transducer placed externally on the patient's body, can be used by the surgeon to monitor the position of the catheter 200 and the probe 300 during the procedure.

As an alternative to using an endoscope to introduce the catheter 200, the catheter 200 could be delivered transcutaneously or through its own cannula. It also is possible to use the catheter 200 in a transcutaneous procedure in which visualization is all that is needed (if the surgeon is highly skilled and experienced). Fluoroscopy also could be used.

As shown in FIG. 2, a sideward-facing exit hole (aperture) 220 is provided adjacent to the distal tip 204 of the catheter 200. The catheter 200 has a hollow interior through which a flexible probe 300 can be moved. As shown in FIG. 2, the distal tip 204 of the catheter 200 is disposed adjacent to one end of the fibroid 50 such that the exit hole 220 of the catheter 200 is positioned adjacent to that one end of the fibroid 50. Accordingly, when the flexible probe 300 is advanced through the hollow interior of the catheter 200, eventually the flexible distal end of the probe 300 exits through the exit hole 220 and is introduced into the fibroid 50 along the major axis of the fibroid 50. Even if the fibroid is substantially spherical instead of ellipsoidal, the disclosed technique, catheter 200 and probe 300 may be used so that the distal end of the probe 300 extends within the fibroid in a direction that is substantially parallel to the uterine wall 14.

Thus, the electrosurgical fibroid ablation system of FIG. 2 includes a catheter 200 and a flexible probe 300. The catheter 200 includes a sharp distal tip 204 configured to pierce tissue such as uterine tissue. The catheter 200 may be rigid or flexible. The catheter 200 also includes a hollow interior and a sideward-facing exit hole 220 located adjacent to the distal tip 204. The catheter includes a guide member (to be discussed below) adjacent to the exit hole 220, with at least a portion of the guide member being located within the hollow interior of the catheter. The flexible probe 300 is movably disposed within the hollow interior of the catheter 200 and includes a distal end 304 that is sufficiently sharp to penetrate through a fibroid. The flexible probe 300 can be moved through the hollow interior of the catheter 200 such that the distal end 304 of the probe 300 can be extended outward of the catheter through the exit hole 220 so as to enter a fibroid when the exit hole of the catheter is positioned adjacent to the fibroid. As will be described further below, the distal end of the probe is flexible and includes at least two electrodes so that the probe can be used to perform bipolar ablation using RFITT. The guide member of the catheter 200 deflects the distal end of the probe when the probe is advanced through the catheter 200 so that the distal end of the probe exits the exit hole 220 at a predefined angle relative to the catheter. In the example shown in FIG. 2, the predefined angle is substantially a right angle. However, according to some embodiments, the guide member is adjustable so that the predefined angle at which the distal end of the probe exits through the exit hole can be adjusted.

Figure 3A:
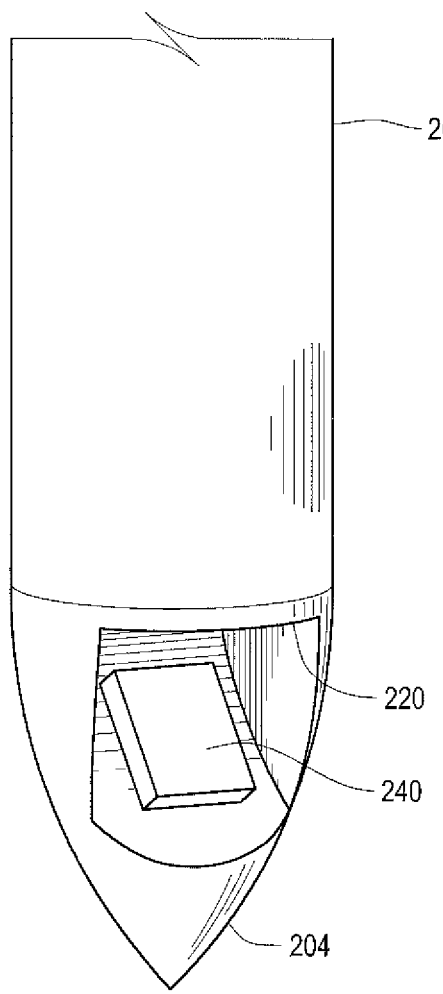
FIGS. 3A and 3B are side views of a catheter according to an embodiment of the invention.
Figure 3B:
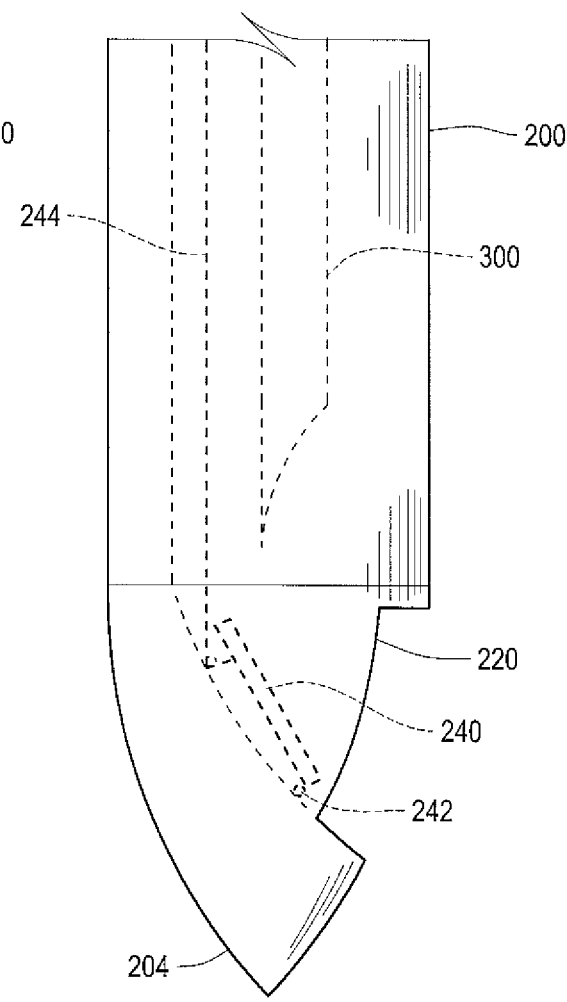

FIGS. 3A and 3B are side views of a catheter 200 having a guide member 240 according to one embodiment. FIG. 3A is a side view of the catheter 200 looking directly into the sideward-facing exit hole 220, whereas FIG. 3B is a side view in which the catheter 200 has been rotated by 90 degrees relative to FIG. 3A.

The guide member 240 in FIGS. 3A and 3B is a plate member 240 that is movably mounted to pivot about a pivot point 242. A linkage mechanism 244 extends from the handpiece of the catheter 200 through the hollow interior of the catheter 200 so that a user can adjust the angle at which the guide member 240 will deflect the distal tip of the probe 300. FIG. 3B shows the probe 300 located entirely within the hollow interior of the catheter 200, that is, in a state before the probe 300 has been moved sufficiently distally so as to contact the guide member 240.

Figure 4:
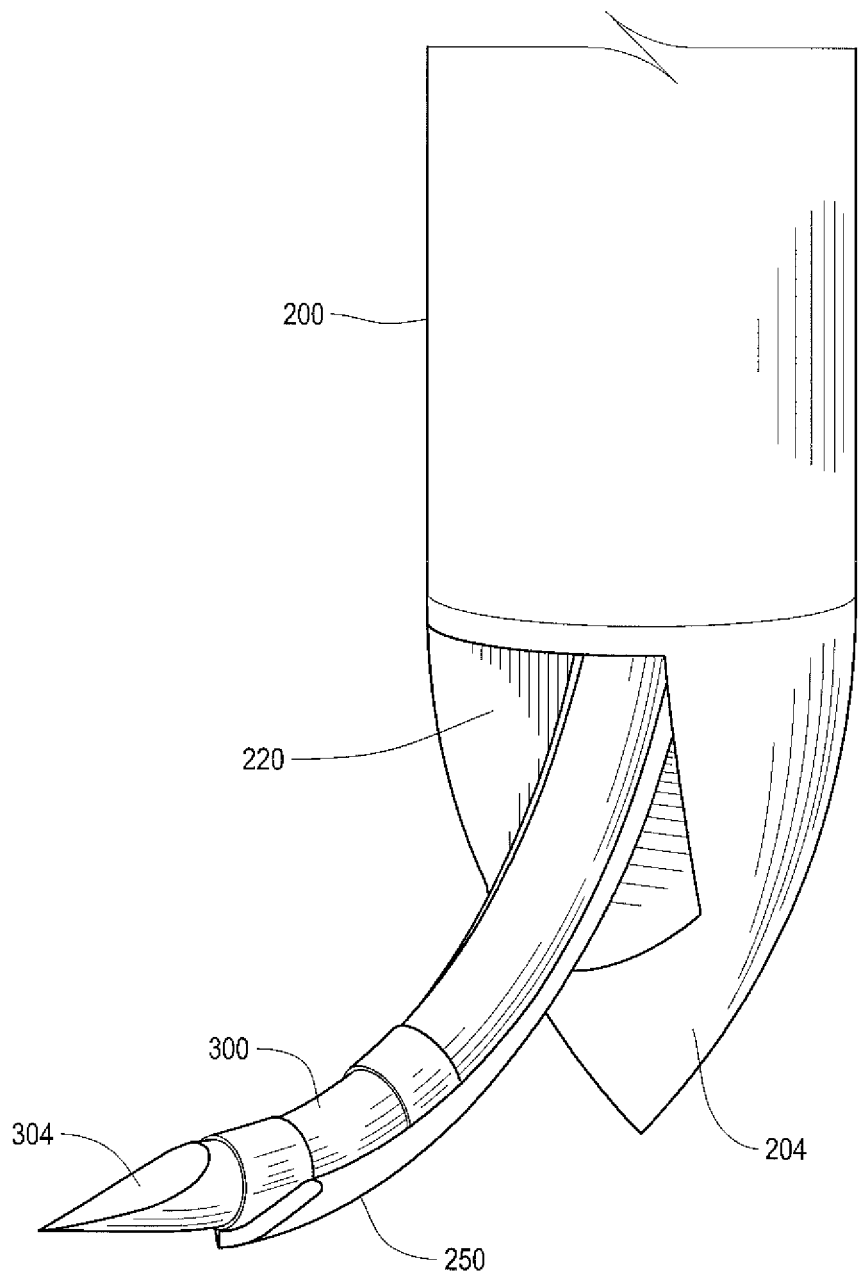
FIG. 4 is a perspective view of a catheter according to an embodiment of the invention.

FIG. 4 is a perspective view of another embodiment of a catheter usable in the invention, and having a different type of guide member. Like the previous embodiments, the catheter 200 includes a sharp distal tip 204 and a sideward-facing exit hole 220 disposed adjacent to the distal tip 204. In the FIG. 4 embodiment, the guide member is a chute or brace 250 having a predetermined bend at its distal end. The angle at which the brace 250 directs the probe 300 will depend on the distance by which the brace 250 has been extended through the exit hole 220. For example, referring to the FIG. 4 embodiment, when the brace 250 extends through the exit hole 220 by a small amount (smaller than what is shown in FIG. 4), the probe 300 will be directed at an angle substantially less than 90 degrees relative to the longitudinal axis of the catheter 200. However, as the chute 250 is advanced further beyond the exit hole 220, it will deflect the distal tip of the probe 300 by a greater amount. As shown in FIG. 4, the chute 250 has been advanced sufficiently far enough to cause the probe 300 to extend at substantially 90 degrees relative to the longitudinal axis of the catheter 200. The chute can be made from a shape-memory material such as, for example, nitinol. The handpiece of the catheter 200 thus would include controls for moving the chute 250 longitudinally within the hollow interior of the catheter 200 and for advancing the probe 300 within the catheter 200 and beyond the exit hole 220.

Figure 5:
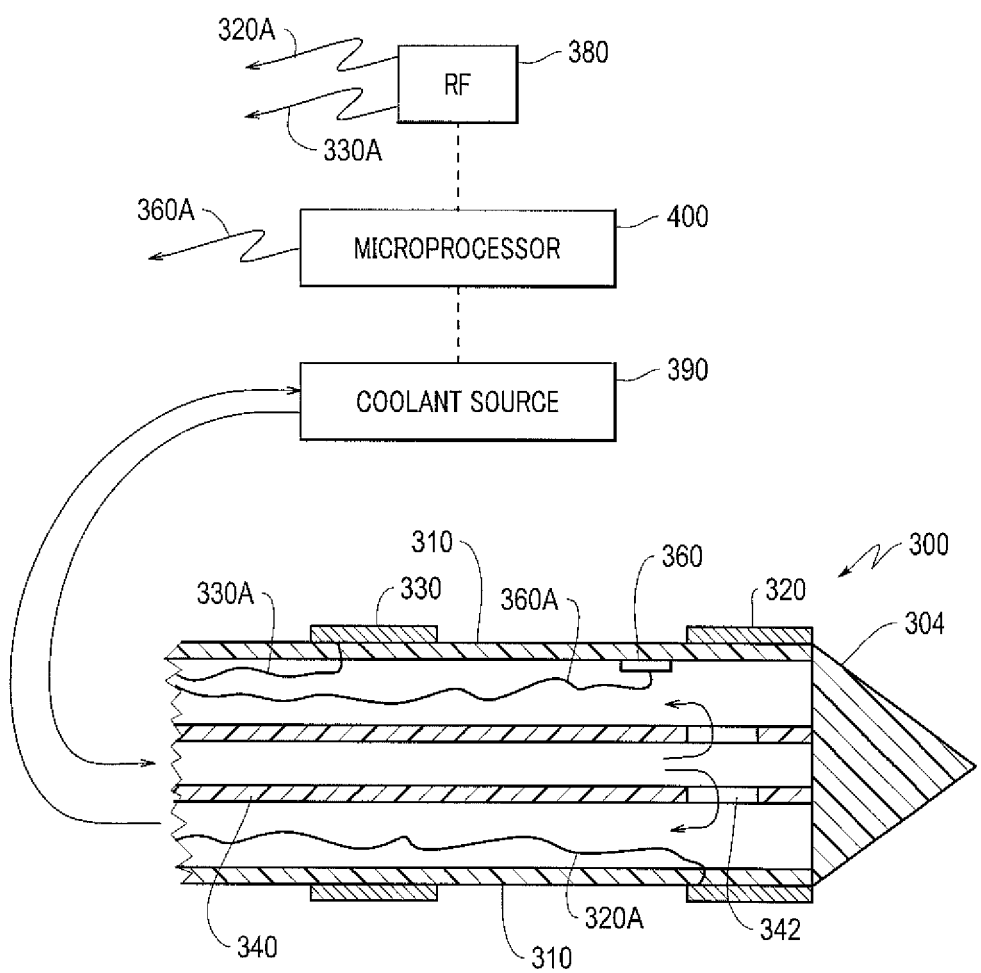
FIG. 5 is a diagram, partly in cross-section, of a bipolar ablation probe according to an embodiment, along with components used with the probe, which include a Radio Frequency generator, cooling system and microprocessor.

FIG. 5 is a diagram of the bipolar ablation probe 300, partially shown in cross-section, along with other components used with the probe 300. Probes and systems suitable for use in RFITT are generally known as shown, for example, in U.S. Pat. No. 6,506,189, U.S. Patent Application Publication No. US2004/0167517, U.S. Patent Application Publication No. US2003/0097130 and U.S. Patent Application Publication No. US2009/0204060, the disclosures of which are incorporated herein by reference in their entireties. U.S. Pat. No. 6,506,189 shows a monopolar probe that thermally ablates living tissue and includes a circulated fluid coolant to cool the contact surface of the probe. The system controls the RF heating energy and the fluid coolant supply based on a sensed temperature of the probe. U.S. Patent Application Publication No. US2004/0167517 discloses a bipolar coagulation probe that is cooled by a liquid. U.S. Patent Application Publication No. US2003/0097130 discloses a fluid cooled bipolar or monopolar probe. U.S. Patent Application Publication No. US2009/0204060 discloses a bipolar probe/catheter that is liquid cooled.

In accordance with the FIG. 5 embodiment, the probe 300 includes an outer flexible tube 310 made from a flexible, electrically-insulative plastic material such as, for example, polytetrafluoroethylene (PTFE) or polyimide. See, for example, U.S. Pat. No. 6,379,349, the disclosure of which is incorporated herein by reference in its entirety. The distal tip 304 of the probe 300 is pointed such that it can penetrate a fibroid. Although tip 304 in the FIG. 5 embodiment is electrically-insulative, and may be made of a material similar to the material from which the tube 310 is made, according to some embodiments, the tip 304 can be an electrically conductive electrode. In the FIG. 5 embodiment, a first electrode 320 is formed adjacent to the distal tip 304, and a second electrode 330 is formed proximally of the first electrode 320. The electrodes 320 and 330 can be formed, for example, by coating an electrically conductive material onto the plastic tube 310. The electrodes 320 and 330 are separated from each other by an electrically-insulative segment of the tube 310. In this regard, the electrodes can be considered to be segments that are movably linked to each other. Electrode 320 includes a conductive lead-line or wire 320A that is attached to a first terminal of a Radio Frequency generator 380. The second electrode 330 includes a lead-line or wire 330A that is attached to a second terminal of the Radio Frequency generator 380. By applying an appropriately modulated signal from the RF generator 380, current will flow from electrode 320 to electrode 330 (or vice versa) through any tissue (i.e., the fibroid) located between those electrodes.

A central coolant-supplying tube 340 is provided through the center of the probe 300 and supplies a cooling fluid (such as water or saline) to the distal tip of the probe. In particular, one or more apertures 342 are provided near the distal end of the tube 340 so that the cooling fluid flows past the internal surface of tube 310. As shown in FIG. 5, a coolant source 390 is coupled to the tube 340 and also receives liquid that has been used to cool the probe from the passage located externally of the tube 340. The liquid can be recirculated or simply discarded once it has been passed through the probe 300. Tube 340 also is flexible and can be made from a plastic material. A temperature sensor 360 such as, for example, a thermocouple, is provided on the internal surface of the tube 310 in the distal area where the electrodes 320 and 330 are located. Temperature sensor 360 is coupled, by lead-line or wire 360A, to a microprocessor 400 so that the microprocessor 400 can sense the temperature at the distal end of the probe. Based on the sensed temperature, microprocessor 400 controls the RF energy generator 380 and the coolant source 390 so as to maintain the distal end of the probe at an appropriate temperature for performing Radio Frequency Induced Thermotherapy. In particular, the temperature is monitored so that the tip of probe 300 (and thus the fibroid tissue adjacent to the tip of probe 300) becomes sufficiently hot so as to ablate the tissue without becoming so hot as to char the tissue, as is well known in RFITT.

Figure 6:
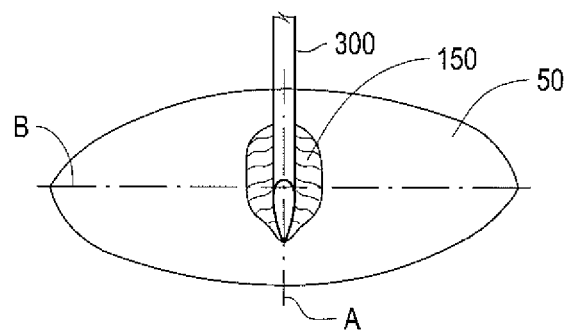
FIG. 6 shows an ablation zone that can be created within an ellipsoidal fibroid when the ablation probe extends in a direction parallel to the minor axis of the fibroid.
Figure 7:
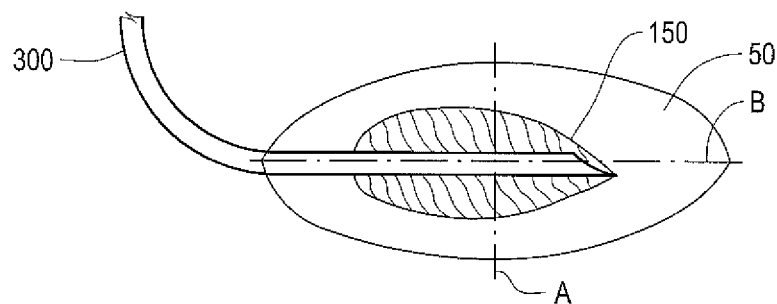
FIG. 7 shows an ablation zone that can be created within an ellipsoidal fibroid when the ablation probe extends in a direction parallel to the major axis of the fibroid.

As mentioned previously, as fibroids grow in size, they become ellipsoidal in shape. FIGS. 6 and 7 show an ellipsoidal fibroid 50 having a minor axis A and a major axis B. FIG. 6 shows the manner in which an ablation zone 150 is formed by a bipolar ablation probe 300 that is inserted into a fibroid 50 so that the axis of the probe is parallel to the minor axis A of the fibroid 50. Although the ablation zone 150 grows outwardly from the probe 300, it does not ablate enough of the fibroid 50 so as to be effective. Accordingly, when the probe is inserted into a fibroid in a direction parallel to the minor axis A, multiple probe insertions must be made along the length of the fibroid 50 (that is, multiple insertions must be made in the direction parallel to the minor axis A) with the multiple insertions being adjacent to each other in the direction of the major axis B.

On the other hand, when the probe 300 is inserted into the fibroid 50 in a direction that is parallel to the major axis B as shown in FIG. 7, the ablation zone 150 is capable of occupying a significant amount of the fibroid 50. The ablation zone 150 also has an ellipsoidal shape that is aligned with the ellipsoidal shape of the fibroid 50. Accordingly, it is possible to ablate the fibroid, even a large ellipsoidal fibroid having a length (in the major axis direction) that is 3-6 cm, with a single insertion of the probe 300 into the fibroid 50. If a fibroid is particularly long in the major axis direction, multiple pairs of bipolar electrodes 320, 330 can be provided along a section of the distal end of the probe 300 so that the size of the ablation zone 150 is increased. Such a change would have little effect if the probe is inserted in a direction parallel to the minor axis A because the shape of the ablation zone 150 in FIG. 6 is not aligned with the shape of the fibroid 50 in FIG. 6.

Thus, and as demonstrated by FIGS. 6 and 7, it is possible to ablate fibroids, even large fibroids, with a single insertion of a bipolar probe into the fibroid if the probe is inserted in a direction that is parallel to the major axis of the ellipsoidal fibroid.

Figure 8:
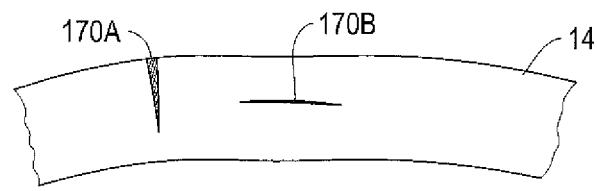
FIG. 8 shows the locations of the uterine wall scars resulting from fibroid ablation with ablation probes inserted in the directions of FIGS. 6 and 7, respectively.

FIG. 8 shows the locations and orientations of uterine wall scars resulting from fibroid ablation with ablation probes inserted in the directions of FIGS. 6 and 7, respectively. In particular, when a probe 300 is inserted into a fibroid such that the electrode is activated to apply ablative energy while the probe extends in a direction perpendicular to the uterine wall (for example, when an ellipsoidal fibroid 50 is ablated in accordance with FIG. 6), a scar 170A shown in FIG. 8 will result. Because scar 170A extends in the thickness direction of the uterine wall, the scar tends to weaken the uterine wall which then becomes prone to propagation (of the scar) and rupture of the uterine wall during pregnancy.

On the other hand, when the probe 300 is activated to apply ablative energy while the probe is extending in a direction substantially parallel to the uterine wall 14 (that is, when an ellipsoidal fibroid is ablated in the manner shown in FIG. 7), a scar such as scar 170B in FIG. 8 results. Because scar 170B extends in a direction that is parallel to the uterine wall (i.e., parallel to the major axis of the ellipsoidal fibroid), the scar is much less likely to propagate and cause rupture of the uterine wall during pregnancy. Thus, uterine ablation in accordance with aspects of the invention can be effective at preserving the uterus and decreasing the risk of uterine rupture during any subsequent pregnancy. The procedure also does not require fibroid extraction and typically does not require suturing of the uterus once the procedure has been completed.

While the procedure has been described with respect to the ablation of ellipsoidal fibroids, it is equally applicable to smaller fibroids that are substantially round. That is, the described embodiments can be used so that the probe 300 extends through a substantially spherical fibroid, with the probe extending through the fibroid in a direction that is substantially parallel to the uterine wall. Again, the catheter 200 would be positioned so that the exit hole 220 of the catheter 200 is disposed adjacent to one end out of two opposite ends of the fibroid, with the two ends being separated from each other in a direction that is substantially parallel to the uterine wall. The probe 300 then would be advanced through the catheter 200 so that the distal end of the probe 300 exits through the exit hole 220 and is introduced into the fibroid in a direction substantially parallel to the wall of the uterus at least until the bipolar electrodes are positioned within the fibroid. The electrodes then would be energized to at least partially ablate the fibroid. Such a technique would be advantageous with substantially spherical fibroids because it also would leave a scar that is parallel to the uterine wall, rather than perpendicular to it.

The illustrated exemplary embodiments are intended to be illustrative and not limiting. Various changes may be made without departing from the spirit and scope of the invention. For example, the method may be performed on other types of uterine fibroids.

What is claimed is:

1. An electrosurgical fibroid ablation system comprising:
    a catheter having (i) a sharp distal tip configured to pierce tissue, (ii) a hollow interior, (iii) a sideward-facing exit hole adjacent to the distal tip, and (iv) a guide member adjacent to the exit hole, at least a portion of the guide member being located within the hollow interior of the catheter; and
    a flexible probe movably disposed within the hollow interior of the catheter and having a distal end that can be extended outward of the catheter through the exit hole so as to enter a fibroid when the exit hole of the catheter is positioned adjacent to the fibroid, the distal end of probe being flexible and including at least two electrodes to perform bipolar ablation,
    wherein the guide member deflects the distal end of the probe when the probe is advanced through the catheter so that the distal end of the probe exits the exit hole at a predefined angle relative to the catheter, and
    wherein the guide member is a pivoting plate that is movably mounted to a pivot point within the catheter to pivot about the pivot point so that the guide member is adjustable to adjust the predefined angle at which the distal end of the probe exits through the exit hole.

2. The system according to claim 1, wherein the probe can be retracted through the exit hole so as to reside entirely within the hollow interior of the catheter.

3. The system according to claim 1, wherein the predefined angle to which the guide member is adjustable to includes approximately a right angle.

4. The system according to claim 1, wherein the pivoting plate resides entirely within the hollow interior of the catheter.

5. The system according to claim 1, wherein the flexible distal end of the probe includes a plurality of segments that are movably linked to each other.

6. The system according to claim 1, wherein the catheter is flexible.

7. The system according to claim 1, wherein the catheter is rigid.

8. An electro surgical fibroid ablation system comprising:
a catheter having (i) a sharp distal tip configured to pierce tissue, (ii) a hollow interior, (iii) a sideward-facing exit hole adjacent to the distal tip, and (iv) a guide member adjacent to the exit hole, at least a portion of the guide member being located within the hollow interior of the catheter; and
a flexible probe movably disposed within the hollow interior of the catheter and having a distal end that can be extended outward of the catheter through the exit hole so as to enter a fibroid when the exit hole of the catheter is positioned adjacent to the fibroid and the distal end of the probe can be retracted through the exit hole so as to reside entirely within the hollow interior of the catheter, the distal end of probe being flexible and including at least two electrodes to perform bipolar ablation,
wherein the guide member deflects the distal end of the probe when the probe is advanced through the catheter so that the distal end of the probe exits the exit hole at a predefined angle relative to the catheter,
wherein the guide member is a pivoting plate that is movably mounted to a pivot point within the catheter to pivot about the pivot point so that the guide member is adjustable to adjust the predefined angle at which the distal end of the probe exits through the exit hole.

9. The system according to claim 8, wherein the guide member can be retracted through the exit hole so as to reside entirely within the hollow interior of the catheter.

10. The system according to claim 8, wherein the catheter is flexible.

11. The system according to claim 8, wherein the catheter is rigid.

* * * * *